United States Patent [19]

Naito

[11] Patent Number: 5,286,641
[45] Date of Patent: Feb. 15, 1994

[54] IN VITRO CULTURE METHOD FOR A FERTILIZED OVUM OF A HEN

[75] Inventor: Mitsuru Naito, Ibaragi, Japan

[73] Assignee: Director General, National Institute of Animal Industry, Ibaragi, Japan

[21] Appl. No.: 761,547

[22] Filed: Sep. 18, 1991

[30] Foreign Application Priority Data

Apr. 30, 1991 [JP] Japan .................................. 3-126657

[51] Int. Cl.$^5$ .......................... C12N 5/00; C12N 1/00
[52] U.S. Cl. .................................. 435/240.1; 435/243
[58] Field of Search ............................. 435/240.1, 243

[56] References Cited

U.S. PATENT DOCUMENTS

| 4,753,928 | 6/1988 | Gutyás et al. | 514/15 |
| 5,011,780 | 4/1991 | Perry | 435/317.1 |

*Primary Examiner*—Douglas W. Robinson
*Assistant Examiner*—Deborah K. Ware
*Attorney, Agent, or Firm*—Nikaido, Marmelstein, Murray & Oram

[57] ABSTRACT

A fertilized ovum is recovered from an upper portion of a magnum of an oviduct of a dead hen 60 to 80 minutes after oviposition. The fertilized ovum is placed in a container containing a thin albumen. A yolk of the ovum is covered with a sheet of gauze, and the ovum is cultured up to the blastoderm stage (stage X) in the container which is covered with a sheet of plastic film that is held by a rubber band.

4 Claims, 1 Drawing Sheet

IN VITRO CULTURE METHOD FOR A FERTILIZED OVUM OF A HEN

BACKGROUND OF THE INVENTION

The present invention relates to an in vitro culture method for culturing a fertilized ovum of a hen.

There is known a culture method where an ovum of a hen which has just been fertilized is submerged in albumen at a temperature of 41° C. for the culture thereof. The ovum can be developed up to an early stage of cell division, but not up to the blastoderm stage (stage X).

In order to culture an undivided fertilized ovum of a hen, the ovum is placed in a glass container filled with a culture medium which is a mixture of thin albumen and salt solution mixed in the ratio of 3:2. The glass container is sealed with a sheet of transparent plastic film. The ovum is thereafter cultured at a temperature between 41° C. and 42° C.

The undivided ovum can thus be developed up to the end of the blastoderm stage (stage X). However, in this case it is necessary to take out the fertilized ovum with sufficiently formed thick albumen from a lower portion of the magnum of oviduct, 165 minutes after the oviposition, or 135 minutes after the ovulation.

The ovum which has just been fertilized is positioned in an upper portion of the magnum of oviduct. At that stage, only mucin albumen and a partical thick albumen are formed around the yolk, so that the fertilized ovum cannot be successfully developed up to the blastoderm stage (stage X) by the culture method mentioned above.

SUMMARY OF THE INVENTION

An object of the present invention is to provide a method of culturing an ovum of a hen wherein a freshly fertilized ovum is developed in vitro up to the blastoderm stage (stage X) so that the embryonic development may be advanced to hatching by combining the recently devised culture method using surrogate eggshells.

According to the present invention there is provided an in vitro culture method for a fertilized ovum of a hen comprising placing the fertilized ovum in a container containing a thin albumen, covering a yolk of the ovum with a sheet of gauze, and culturing the ovum up to the blastoderm stage (stage X).

In an aspect of the invention, the ovum in the container is positioned such that a germinal disk is located at a top of the yolk. The fertilized ovum is taken out from an upper portion of the magnum of oviduct of a hen.

The other objects and features of this invention will become understood from the following description with reference to the accompanying drawings.

DETAILED DESCRIPTION OF THE PREFERRED EMBODIMENT

Figure 1:
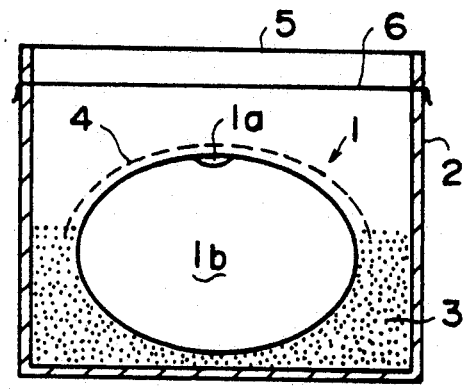
FIG. 1 is a sectional elevational view showing an ovum in a container to which the in vitro method according to the present invention is applied.
Figure 2:
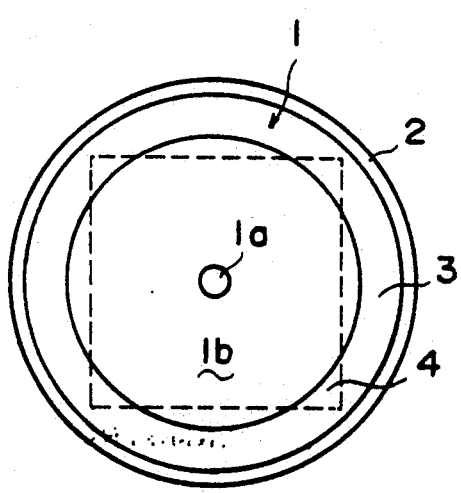
FIG. 2 is a plan view of the container of FIG. 1.

Referring to the drawings, an ovum (embryo) 1 which has just been fertilized is taken out from an upper portion of the magnum of oviduct of a dead hen, 60 to 80 minutes after the oviposition, or 30 to 40 minutes after the ovulation. As shown in FIGS. 1 and 2, the ovum 1 is placed in a glass container 2 having an inner diameter of 45 mm and a height of 50 mm, and 5 ml of thin albumen 3 which is divided from oviposited eggs is poured into the container 2.

A yolk 1b of the ovum 1 is rotated so that the germinal disk 1a is located at an upward position 1b. A sheet of gauze 4 of three centimeters square is so disposed as to cover the yolk 1b including the germinal disk 1a. The four corners of the gauze 4 is soaked in the surrounding thin albumen 3. The opening of the glass container 2 is covered with a sheet of plastic film 5 which is held by a rubber band 6 to seal the opening of the container 2. The ovum 1 is cultured in this condition for 26 hours at the temperature of 41.5° C.

The ovum 1 is cultured by the method of the present invention up to the blastoderm stage (stage X). The ovum 1 is thereafter cultured by the recently devised method using surrogate eggshells to hatching.

The following table shows the viability and the hatching rate of the fertilized ovum by the method of the present invention up to the blastoderm stage (stage X), and further by the known methods after blastoderm stage. The table further indicates, for comparison, the results obtained with laid eggs cultured by the recently devised culture method. Thus, the yolk 1b is covered with a film of the thin albumen soaked in the gauze, so that the yolk is prevented from drying.

TABLE

Viability and Hatching Rate of Ovum of Hen

| Number of Days After Ovulation | Present Invention | Laid Egg |
|---|---|---|
| 0 | n = 82 | |
| 1 | . | n = 44 |
| 2 | | |
| 3 | . | . |
| 4 | 46.3 | 100.0 |
| 5 | 32.9 | 100.0 |
| 6 | 32.9 | 97.7 |
| 7 | 31.7 | 97.7 |
| 8 | 30.5 | 93.2 |
| 9 | 30.5 | 93.2 |
| 10 | 30.5 | 93.2 |
| 11 | 30.5 | 93.2 |
| 12 | 30.5 | 93.2 |
| 13 | 30.5 | 93.2 |
| 14 | 30.5 | 93.2 |
| 15 | 30.5 | 93.2 |
| 16 | 30.5 | 93.2 |
| 17 | 30.5 | 93.2 |
| 18 | 30.5 | 90.9 |
| 19 | 30.5 | 86.4 |
| 20 | 30.5 | 84.1 |
| 21 | 30.5 | 79.5 |
| 22 | 24.4 | 68.2 |
| Hatch | 19.5 | 43.2 |

As shown in the table, at least 46.3% of the fertilized ova cultured by the method of the present invention have developed to the blastoderm stage (stage X), and 19.5% have hatched.

From the foregoing it will be understood that the present invention provides a method of culturing a fertilized ovum wherein the ovum is developed to the blastoderm stage (stage X) by the in vitro culture starting immediately after the fertilization.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An in vitro culture method for a fertilized ovum of a hen comprising:

recovering a fertilized ovum from an upper portion of a magnum of an oviduct of a dead hen 60 to 80 minutes after oviposition;

providing thin albumen in a container having sufficient capacity to hold said fertilized ovum and a sufficient amount of said thin albumen to partially submerge said fertilized ovum;

placing said fertilized ovum in said container and partially submerging said fertilized ovum in said thin albumen whereby effectively contacting said fertilized ovum with said thin albumen in said container;

covering a yolk of the ovum with a sheet of gauze which is in effective contact with said thin albumen and with said yolk; and culturing the ovum so covered with said gauze up to the blastoderm stage.

2. The method according to claim 1 wherein the ovum in the container is positioned such that a germinal disk is located in an upward position.

3. The method according to claim 1 wherein an upper opening of the container is covered with a sheet of plastic film which is held by a rubber band.

4. The method according to claim 1 wherein the ovum is cultured for 26 hours at a temperature of 41° C. to 42° C.

* * * * *

UNITED STATES PATENT AND TRADEMARK OFFICE
CERTIFICATE OF CORRECTION

PATENT NO. : 5,286,641
DATED : February 15, 1994
INVENTOR(S) : Mitsuru Naito et al It is certified that error appears in the above-indentified patent and that said Letters Patent is hereby corrected as shown below:

On the title page, Item [75], after "Naito", insert --Keijiro Nirasawa, Takao Oishi, all of --.

Signed and Sealed this

Twenty-ninth Day of November, 1994

*Attest:*

BRUCE LEHMAN

*Attesting Officer*     *Commissioner of Patents and Trademarks*